United States Patent [19]

Nguyen

[11] Patent Number: 5,897,865
[45] Date of Patent: Apr. 27, 1999

[54] TURMERIC FOR TREATING SKIN DISORDERS

[76] Inventor: Van Bich Nguyen, 927 Eastham Ct., #24, Crofton, Md. 21114

[21] Appl. No.: 08/885,867

[22] Filed: Jun. 30, 1997

[51] Int. Cl.⁶ .......................... A61K 35/78; A61K 39/385
[52] U.S. Cl. ......................................... 514/195.1; 514/859
[58] Field of Search .......................... 424/195.1; 514/859

[56] References Cited

U.S. PATENT DOCUMENTS 5,401,504   3/1995   Das et al. .............................. 424/195.1

OTHER PUBLICATIONS

Chemical Abstracts vol. 117:162945u (Conney et al.), 1992.
Chemical Abstracts vol. 123:265808j (Oosawa et al.), 1995.

*Primary Examiner*—Leonard Schenkman
*Attorney, Agent, or Firm*—Millen, White, Zelano & Branigan, P.C.

[57] ABSTRACT

The present invention relates to the administration of an effective amount of turmeric for the treatment of various health ailments and also as a food supplement to promote health and vitality. The turmeric is especially useful for the treatment of skin disorders, such as acne, when administered orally. It can also be used to treat liver and stomach disorders, skin discoloration, constipation, and hemorrhoids.

4 Claims, No Drawings

TURMERIC FOR TREATING SKIN DISORDERS

BACKGROUND OF THE INVENTION

Turmeric has been used as a cooking spice and traditional medicine for many years, especially in Asian countries. See, e.g., U.S. Pat. No. 5,401,594. The following disclosure describes an effective treatment protocol for various diseases and other health ailments.

SUMMARY OF THE INVENTION

The present invention relates to the treatment of medical disorders and ailments comprising the administration of an effective amount of turmeric. Various disorders and ailments can be treated in accordance with the present invention, including skin conditions, gastrointestinal disturbances, pain, and other medically troublesome disorders. Treatment with turmeric is an effective method to achieve rapid relief naturally. In another aspect of the invention, turmeric is utilized prophylactically as a dietary supplement to promote health and a sense of well-being.

Skin conditions that can be treated with turmeric include acne and other skin conditions, especially those associated with blemishes or pimples. Acne types that can be treated include, e.g., artificialis, atrophica, cachecticorum, ciliaris, conglobata, decalvans, indurata, keloid, urticaria, varioliformis, and vulgaris. To enhance the effect of turmeric, a short exposure to natural or artificial (e.g., 20 minutes in a conventional tanning bed) sun can be employed. Turmeric is also a beneficial therapy for skin conditions that arise during childhood and adolescence, e.g., as a consequence of puberty or other physiological changes in body chemistry that occur during maturation. Turmeric is also used to heal skin, e.g., caused by the normal aging process, sun exposure, contact with environmental irritants, including pollution, smoke, and ozone. After the administration of turmeric, the skin is restored to a healthier and smoother appearance having improved texture and resilience. Turmeric can also be employed to restore skin color to its normal hue when discolored. In accordance with the present invention, the skin disorders are preferably treated by administering turmeric orally.

In addition, gastrointestinal and other internal disturbances can be treated in accordance with the present invention. For example, stomach disorders can be treated by administering turmeric. The stomach disorders include, e.g., infections caused by bacteria and other pathogenic organisms, sour stomach, alcohol-related ailments, ulcers, and pain. Liver ailments are also treatable in accordance with the invention, e.g., pain, infections, jaundice, cancer, and alcohol-related disturbances. Turmeric is also useful to treat hemorrhoids, e.g., by promoting healing, eliminating pain, and stopping or slowing bleeding. Constipation can also be relieved treated by administering turmeric, especially in the oral doses described below. Turmeric is also useful for eliminating body odors, such as those produced by stomach acidity.

An effective amount of turmeric can be administered prophylactically to prevent the recurrence of any of the above-mentioned disorders and ailments. For example, in the case of acne associated with adolescence, a prophylactic dose of turmeric can be orally administered on a daily basis. Once a patient having a skin condition is treated and cured, the patient can continue to ingest turmeric, e.g., 500 mg to 5 gm, preferably 2 gram, per day, to promote healthy skin and deter further acne. Turmeric is also used to promote healthy and vitality, e.g., as an anti-oxidant, anti-carcinogen, and anti-bacterial agent. for such use, the turmeric can be administered in amounts of, e.g., e.g., 500 mg to 5 gmn, preferably 2 gram, per day.

An effective amount of turmeric is administered to a host who is to be treated. An effective amount is a quantity of turmeric which produces the desired effect, e.g., which treats (e.g., ameliorates) the skin disorder, hemorrhoids, constipation, liver disorder, stomach ailment, or gastrointestinal disorder. The turmeric is generally administered from about 250 milligrams to 10 grams per day, preferably about 2–4 gram per day. In one treatment regime, about 1 gram of turmeric is administered in the first day, and 2 grams of turmeric is administered on subsequent days, e.g, until the condition is ameliorated, e.g., from about 2–4 days. Thus, about 7 grams is administered in a single treatment regime. The turmeric is preferably administered as a soft gel containing 500 mg turmeric with 8 ounces of water. For example, an adult to be treated in accordance with the present invention can take two soft gels (e.g., 1 gram), twice a day with a cup of water. The effective amount of turmeric can be administered in the morning (with breakfast) and in the afternoon (with lunch). The turmeric is administered preferably a meal time. Children from about 12 to 16 years of age can be treated with turmeric, but with half the dosage used for an adult human. Before starting the treatment regime, a patient should be tested for food allergy or other contraindications by ingesting a small quantity of turmeric. It is especially preferred that the turmeric is administered along with large quantities of water, e.g., a standard cup of water. It is recommended that the host cleanse his stomach one day before treatment by abstaining from the ingestion of meat, vegetables, and fruits. The same dosages are applicable when turmeric is used as a dietary supplement.

Turmeric is a member of the family Zingiberaceae. It is generally obtained from the rhizome of the plant *Curcuma loga*. Turmeric can be obtained from various sources, including commercially available sources. Various forms of turmeric can be utilized in accordance with the present invention, including fresh, powdered, liquid juice, pulp, or resin. The amounts of turmeric discussed herein refer to grams per dry weight of powder. When pulp or liquid turmeric is utilized, the amount of turmeric is calculated based on the weight of the starting material. When fresh turmeric is utilized, the effective amounts are about 3–10 times the amount for powdered turmeric. The amounts recited in this application refer to powdered turmeric.

Turmeric in accordance with the present invention, optionally with other active or inactive agents, can be administered by various routes, e.g., enteral, parenteral, oral, nasal, rectal, intervenous (e.g., using a catheter), subcutaneous, sublingual, buccal, topical, intramuscular, by inhalation, percutaneous, vaginal, intra-arterial, intradermal, epidural, systemically, topical, intraperitoneal, intrapleural, etc. Endoscopic injections of gastrointestinal regions, as well as suppository treatments can also be used.

Turmeric can be formulated as a oral or topical preparation by bringing it into a suitable dose form, e.g., together with an excipient or auxiliary, and, if desired, with one or more further active compounds. The preparations can be utilized in both human and veterinary medicine. Suitable excipient include, e.g., organic and inorganic substances which are appropriate for enteral, parenteral, or oral administration, e.g., water, saline, buffers, vegetable oils, mineral oils, benzyl alcohol, cyclodextrin, hydroxypropyl-cyclodextrin (especially beta-type), polyethylene glycols, glycerol triacetate and other fatty acid glycerides, gelatin, soya lecithin, carbohydrates such as lactose or starch or other sugars, magnesium stearate, talc or cellulose. The preparations can be sterilized and/or contain additives, such as preservatives or stabilizers. Turmeric can be formulated with various oils, including coconut, sunflower, mustard, almond, sesame, safflower, or peanut. For a soft gel, powdered turmeric can be combined with a syrup, e.g., a sugar-based syrup.

Turmeric can be formulated with various active agents, e.g., vitamin E, tocopheryl acetate, calcium. Turmeric can also be formulated with other herbs and plants, depending on the desired purpose and effect. These herbs and plants include, ginger, garlic, fenugreek, guava leaves, *Aquilaria agallocha, Ficus racemosa, Saraca asoka, Trigionell foenum-graecum, Curcuma aromatica, Meriandra bengalensis, Zanthoxylum budrunga, Withania somnifera, Crocus sativus, Saussurea lappa*. And for haircase: *Eclipta alba, Bacopa monnieri, Sida retusa, Indigofera tinctoria, Cardiospermum halicacabum, Hibiscus rosa-sinensis*. Other plants and herbs include those mentioned in various text and publications, e.g., E S Ayensu, Medicinal Plants of West Africa, Reference Publications, Algonac, Mich. (1978); P. Back, The Illustrated Herbal 1987, Hamlyn Publishers, distributed by Octopus Books, Printed in Hong Kong by Mandarin, ISBN 0-600 553 361; F. Bianchini and F. Corbetta, The Fruits of the Earth, translated from Italian by A. Mancinelli, Bloomsbury Books, London, ISBN 1-870630-10-6; H. M. Burkill, The Useful plants of West Tropical Africa, Ed. 2, V. I, Royal Botanic Gardens Kew, ISBN 0-947643-01-X (1985); L. Boulos, Medicinal Plants of North Africa, Reference Publications Inc., Algonac, Mich. (1983); and N. C. Shah, Herbal folk medicines in Northern India, J. Ethnopharm, 6:294–295 (1982). The turmeric can also be formulated with components as described in CN 1098926 and JP 7309713.

Turmeric can also be formulated into topical preparations. A preferred preparation comprises turmeric powder, water, mineral oil, vitamin E, methylparaben, and propylene glycol. The turmeric powder can be mixed with commercialiy-available vitamin E cream. Other ingredients that can be combined in a topical preparation include, sodium lauryl sulfate, oleanic acid, linoleamide DEA, glycol stearate, stearic acid, sodium hydroide, trisodium EDTA, tetrasodium EDTA, alcohols, polyethylene glycols, fragrances, preservatives, deionized water, dimethicone, glycerin, antibacterials, and other ingredients that the skilled worker would know.

The turmeric can also be co-administered with other active agents to achieve synergistic effects. For example, the turmeric can be co-administered with an antibiotic for the treatment of any of the above-mentioned disorders, such as acne. Other active agents include, e.g., antioxidants, anticarcinogens, antiinflammatory agents, hormones and hormone antagonists, antibiotics (e.g., amoxicillin) and other bacterial agents, and other medically useful drugs such as those identified in, e.g., *Remington's Pharmaceutical Sciences*, Eighteenth Edition, Mack Publishing Company, 1990.

Health problems which are treatable in accordance with the invention can be produced and/or exacerbated, for example, by coffee, cigarette or cigar smoke, spicy foods, oils, alcohol, and other dietary irritants. The turmeric treatment described here is generally most beneficial if such irritating factors are eliminated from the diet. Furthermore, the treatment is enhanced if a patient obtains fresh air and sunshine, especially the morning sun. One optimal turmeric regime requires four days of treatment. On the first day of treatment, one gram is administered to the host in the morning in an oral dosage form. Two grams of turmeric (e.g., one gram with breakfast and one gram with lunch) is administered subsequently for three additional days. At the end of such period, treatment is generally accomplished and the disorder is relieved. However, if a patient continues to consume dietary and health irritants, the treatment can require additional days and/or turmeric dosages. For example, if the host continues to smoke, then at least one additional day and one additional gram per day is recommended. Optimally, the host will refrain from the following activities: drinking coffee and alcohol, eating butter, or other oils, and spicy foods (e.g., containing hot red pepper or black pepper), and smoking.

Other foods which are preferably ingested during the treatment period include, white rice, soup, noodles, yam, white potato, egg whites, bread, corn, oat meal, and cereals. Liquid foods include, milk, fresh orange juice, tomato juice, ginseng tea, light tea, and apply juice. A preferred meal includes a sirloin steak in combination with potatoes or rice or bread, and a salad containing lettuce, carrot, tomato, watercress, and/or radish. Barbecued meats, such as pork, chicken, beef, or food, can also be eaten but these can not be spicy and should be eaten with rice, potato, noodles, or bread.

Seafood can also be eaten during the turmeric treatment regime. Preferred seafoods include oysters (eaten fresh with lemon, salt, and black pepper or cooked lightly), shrimp (cooked well), or crab. The crab should be large sized, but not jumbo, and should not be served with hot spices. The seafood is eaten preferably with corn, potatoes, rice, noodles, and/or bread.

Soups are also a preferred part of the diet to be consumes during the turmeric regime. The soup can be prepared with chicken, pork, or beef. Preferably, the soup is a clear broth with a small amount of ginger, onion, leek, green onion, sugar, and/or salt for flavoring. Rice can added to the soup to improve its quality.

Vegetables eaten during the administration of turmeric should be simple and not mixed, e.g., cooked green beans (use large quantities of water), small cab, squash, potatoes, yam, and corn. Fruits that can eaten include, e.g., orange, grape, apple, plum, and banana.

EXAMPLE

A 15-year old female was treated for facial and body acne. The turmeric was prepared in the form of a soft gel by combining 500 mg of powdered turmeric (obtained from a commercial grocery) and sugar syrup. Two grams of turmeric was administered to the patients daily for three days: one gram was ingested at breakfast and one gram at dinner. On the fourth day, the facial and body acne was noticeably diminished. By the seventh day, the skin was clear.

The preceding examples can be repeated with similar success by substituting the generically or specifically described reactants and/or operating conditions of this invention for those used in the preceding examples.

The entire disclosure of all applications, patents and publications, cited above, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed:

1. A method of treating acne comprising, administering orally an effective amount of turmeric to a subject having acne.

2. A method of claim 1, wherein the amount of turmeric administered is at least 500 mg per day.

3. A method of claim 1, wherein the amount of turmeric administered is at least 2 grams per day.

4. A method of claim 1, wherein 1 gm of turmeric is administered on the first day of treatment and 2 gm of turmeric is administered on the second, third, and fourth day of treatment.

* * * * *